US010279134B2

(12) United States Patent
 Kwok

(10) Patent No.: US 10,279,134 B2
(45) Date of Patent: May 7, 2019

(54) RECOGNITION SYSTEM FOR AN APPARATUS THAT DELIVERS BREATHABLE GAS TO A PATIENT

(71) Applicant: ResMed Limited, Bella Vista, New South Wales (AU)

(72) Inventor: Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 860 days.

(21) Appl. No.: 14/862,596

(22) Filed: Sep. 23, 2015

(65) Prior Publication Data

US 2016/0008560 A1   Jan. 14, 2016

Related U.S. Application Data

(60) Continuation of application No. 13/588,556, filed on Aug. 17, 2012, now Pat. No. 9,162,035, which is a
(Continued)

(51) Int. Cl.
*A61M 16/00* (2006.01)
*A61M 16/08* (2006.01)
*A61M 16/16* (2006.01)

(52) U.S. Cl.
CPC .... *A61M 16/0066* (2013.01); *A61M 16/0069* (2014.02); *A61M 16/0816* (2013.01); *A61M 16/0875* (2013.01); *A61M 16/16* (2013.01); *A61M 2205/15* (2013.01); *A61M 2205/3334* (2013.01); *A61M 2205/60* (2013.01);
(Continued)

(58) Field of Classification Search
CPC .......... A61M 16/0066; A61M 16/0069; A61M 16/0816; A61M 16/0875; A61M 16/16; A61M 2205/60; A61M 2205/3334; A61M 16/6027; A61M 16/6018; A61M 16/6045
See application file for complete search history.

(56) References Cited

U.S. PATENT DOCUMENTS 2,598,978 A   6/1952   Martin
4,695,955 A   9/1987   Faisandier
(Continued)

FOREIGN PATENT DOCUMENTS

DE   40 20 522   1/1992
EP   1 127 583   8/2001
(Continued)

OTHER PUBLICATIONS

Second Amended Counterstatement in NZ Application No. 700746 dated Dec. 12, 2017 (17 pages).
(Continued)

*Primary Examiner* — Gregory A Anderson
*Assistant Examiner* — Margaret M Luarca
(74) *Attorney, Agent, or Firm* — Nixon & Vanderhye P.C.

(57) ABSTRACT

An adapter for use with a flow generator includes a conduit attachable to the outlet of the flow generator and an identifying element supported by the conduit and providing an identifying feature unique to a specific peripheral component attachable to the flow generator. The identifying feature is communicatable to the flow generator so that appropriate operating parameters of the flow generator may be automatically selected by the flow generator to coordinate with the specific peripheral component.

12 Claims, 11 Drawing Sheets

Related U.S. Application Data division of application No. 11/794,150, filed as application No. PCT/AU2006/000238 on Feb. 24, 2006, now Pat. No. 8,267,084.

(60) Provisional application No. 60/656,880, filed on Mar. 1, 2005.

(52) U.S. Cl.
CPC ............ *A61M 2205/6018* (2013.01); *A61M 2205/6027* (2013.01); *A61M 2205/6045* (2013.01)

(56) References Cited

U.S. PATENT DOCUMENTS

| | | |
|---|---|---|
| 4,768,496 A | 9/1988 | Kreizman et al. |
| 4,883,051 A | 11/1989 | Westenskow |
| 4,944,310 A | 7/1990 | Sullivan |
| 5,072,728 A | 12/1991 | Pasternack |
| 5,293,865 A * | 3/1994 | Altner ............... A61M 16/186 128/202.27 |
| 5,413,097 A | 5/1995 | Birenhelde et al. |
| 5,490,502 A | 2/1996 | Rapoport et al. |
| 5,503,146 A | 4/1996 | Froehlich et al. |
| 5,660,567 A | 8/1997 | Nierlich et al. |
| 5,813,404 A | 9/1998 | Devlin et al. |
| 5,844,862 A | 12/1998 | Cocatre-Zilgien |
| 5,895,595 A | 4/1999 | Haden |
| 5,950,621 A | 9/1999 | Klockseth |
| 6,035,851 A | 3/2000 | Wallen |
| 6,085,747 A | 7/2000 | Axe et al. |
| 6,119,686 A | 9/2000 | Somerson et al. |
| 6,126,610 A | 10/2000 | Rich et al. |
| 6,142,949 A | 11/2000 | Ubby |
| 6,158,430 A | 12/2000 | Pfeiffer et al. |
| 6,186,140 B1 | 2/2001 | Hoague |
| 6,360,741 B2 | 3/2002 | Truschel |
| 6,363,933 B1 | 4/2002 | Berthon-Jones |
| 6,425,395 B1 | 7/2002 | Brewer et al. |
| 6,546,930 B1 | 4/2003 | Emerson et al. |
| 6,678,215 B1 | 1/2004 | Treyz et al. |
| 6,910,483 B2 | 6/2005 | Daly et al. |
| 6,953,354 B2 | 10/2005 | Edirisuriya et al. |
| 7,148,806 B2 | 12/2006 | Antitila |
| 7,314,451 B2 | 1/2008 | Halperin et al. |
| RE40,365 E | 6/2008 | Kirchgeorg et al. |
| 7,424,889 B2 | 9/2008 | Mashak |
| 7,469,698 B1 | 12/2008 | Childers et al. |
| 7,527,053 B2 | 5/2009 | DeVries et al. |
| 7,607,437 B2 | 10/2009 | Boyle et al. |
| 7,891,353 B2 | 2/2011 | Chalvignac |
| 7,913,689 B2 | 3/2011 | Henry et al. |
| 7,987,847 B2 | 8/2011 | Wickham et al. |
| 7,997,885 B2 | 8/2011 | Allum |
| 8,006,691 B2 | 8/2011 | Kenyon et al. |
| 8,186,345 B2 | 5/2012 | Payton et al. |
| 8,210,173 B2 | 7/2012 | Schermeier et al. |
| 8,267,084 B2 | 9/2012 | Kwok |
| 8,381,725 B2 | 2/2013 | Chalvignac |
| 8,424,514 B2 | 4/2013 | Oates |
| 9,162,035 B2 | 10/2015 | Kwok |
| 2001/0017134 A1 | 8/2001 | Bahr |
| 2002/0022973 A1 | 2/2002 | Sun et al. |
| 2002/0088464 A1 | 7/2002 | Truschel |
| 2002/0144682 A1 | 10/2002 | Kurger et al. |
| 2002/0174867 A1 | 11/2002 | Gunaratnam et al. |
| 2003/0076745 A1 | 4/2003 | Chapman |
| 2003/0140924 A1 | 7/2003 | Aylsworth et al. |
| 2003/0154981 A1 | 8/2003 | Spruiell |
| 2003/0187525 A1 | 10/2003 | Mann et al. |
| 2003/0196662 A1 | 10/2003 | Ging et al. |
| 2003/0208465 A1 | 11/2003 | Yurko et al. |
| 2003/0236450 A1 | 12/2003 | Kocinski |
| 2004/0074495 A1 | 4/2004 | Wickham et al. |
| 2004/0118403 A1 | 6/2004 | O'Connor et al. |
| 2004/0163647 A1 | 8/2004 | Figley et al. |
| 2004/0171982 A1 | 9/2004 | Danchin |
| 2004/0182386 A1 | 9/2004 | Meier |
| 2004/0210151 A1 | 10/2004 | Tsukashima et al. |
| 2004/0226566 A1 | 11/2004 | Gunaratnam et al. |
| 2005/0061318 A1 | 3/2005 | Faram |
| 2005/0076906 A1 | 4/2005 | Johnson |
| 2005/0114182 A1 | 5/2005 | Randolph et al. |
| 2005/0211761 A1 | 9/2005 | Anttila et al. |
| 2006/0231092 A1 | 10/2006 | Mashak |
| 2006/0278220 A1 | 12/2006 | Schermeier et al. |
| 2007/0000491 A1 | 1/2007 | Chalvignac |
| 2007/0144519 A1 | 6/2007 | Henry |
| 2008/0078387 A1 | 4/2008 | Vandine |
| 2009/0120437 A1 | 5/2009 | Oates |
| 2010/0147301 A1 | 7/2010 | Kwok |
| 2010/0236552 A1 | 9/2010 | Kwok et al. |
| 2011/0139153 A1 | 6/2011 | Chalvignac |
| 2011/0139154 A1 | 6/2011 | Henry et al. |
| 2012/0304994 A1 | 12/2012 | Kwok |
| 2012/0318266 A1 | 12/2012 | Chou |
| 2013/0206143 A1 | 8/2013 | Oates et al. |

FOREIGN PATENT DOCUMENTS

| | | |
|---|---|---|
| EP | 1127583 | 7/2003 |
| EP | 1 449 558 | 8/2004 |
| EP | 1 516 641 | 3/2005 |
| EP | 1 579 884 | 9/2005 |
| JP | H04-158856 | 6/1992 |
| JP | 6-23051 | 2/1994 |
| JP | 2002-172170 | 6/2002 |
| JP | 2003-061977 | 3/2003 |
| JP | 2004-532666 | 10/2004 |
| WO | WO 96/28093 | 9/1996 |
| WO | 1997/006843 | 2/1997 |
| WO | 2001/000264 | 1/2001 |
| WO | 2001/32069 | 5/2001 |
| WO | 2001-91841 | 12/2001 |
| WO | 2002/053217 | 7/2002 |
| WO | 2004/049912 | 6/2004 |
| WO | 2004-060443 | 7/2004 |
| WO | 2004-112873 | 12/2004 |
| WO | 2005/002655 | 1/2005 |
| WO | 2005/011556 | 2/2005 |
| WO | WO 2005/037355 | 4/2005 |
| WO | 2005/067520 | 7/2005 |
| WO | WO 2006/092001 | 9/2006 |
| WO | 2006-125252 | 11/2006 |
| WO | 2007-059810 | 3/2007 |
| WO | WO 2007/041797 | 4/2007 |

OTHER PUBLICATIONS

Letter from The New Zealand Intellectual Property Office dated Jan. 26, 2016, granting an Extension of Time and forwarding an Application for Extension of Time and a Notice of Opposition to Grant of Patent (Section 21) filed Jan. 25, 2016, in a related New Zealand Application No. 700746, and (4 pages).
A Statement of Case filed Mar. 29, 2016, in a related New Zealand Application No. 700746 (16 pages).
Letter from the New Zealand Intellectual Property Office dated Apr. 1, 2016, forwarding a First Amended Notice of Opposition to Grant of Patent (Section 21) filed Mar. 29, 2016, in a related New Zealand Application No. 700746 (3 pages).
Affirmation of Ian Douglas Makinson, Mar. 3, 2017 (312 pages).
Affirmation of Alex Young, Mar. 3, 2017 (12 pages).
Affirmation of Craig Seddon Rothwell, Mar. 3, 2017 (64 pages).
Amended Statement of Case filed Feb. 3, 2017 (17 pages).
Affirmation of Ian Douglas Makinson, Jan. 26, 2017 (14 pages).
Affirmation of Andrew Baden Clark, Feb. 3, 2017 (14 pages).
Affirmation of Andrew Michael Baker, Feb. 3, 2017 (26 pages).
Amended Counterstatement, Jun. 26, 2017, (14 pages).
Claims filed in New Zealand Application No. 700746, Jun. 26, 2017 (3 pages).

(56) References Cited

OTHER PUBLICATIONS

Amended Notice of Opposition to Grant of Patent and Statement of Case issued Feb. 29, 2012 for corresponding New Zealand Application No. 567371.
International Search Report for PCT/AU2006/001506 dated Jan. 30, 2007.
Written Opinion of the International Searching Authority for PCT/AU2006/001506, dated Jan. 30, 2007.
International Preliminary Report on Patentability for PCT/AU2006/001506, dated Jan. 30, 2007.
Amended Notice of Opposition to Grant a Patent, filed on Jan. 28, 2014 in New Zealand Application No. 591993.
Statement of Case, filed on Jan. 28, 2014 in New Zealand Application No. 591993.
"Alarm Clock" The Penguin English Dictionary. 2007. http://www.credoreference.com/entry/penguineng/alarm_clock (Sep. 30, 2013).
Second Amended Notice of Opposition to Grant a Patent, filed on Jul. 18, 2014 in New Zealand Application No. 591993.
Amended Statement of Case, filed on Jul. 18, 2014 in New Zealand Application No. 591993.
Second Amended Statement of Case, filed on Sep. 29, 2014 in New Zealand Application No. 591993.
Statutory Declaration of Alex Young filed on Sep. 29, 2014 in New Zealand Application No. 591993.
Statutory Declaration of Andrew Baden Clark filed on Sep. 29, 2014 in New Zealand Application No. 591993.
Statutory Declaration of David Robin Whiting filed on Sep. 29, 2014 in New Zealand Application No. 591993.
Amended Counterstatement, filed on Aug. 21, 2014 in New Zealand Application No. 591993.
Statutory Declaration of Andrew Baden Clark, filed on Sep. 8, 2014 in New Zealand Application No. 600480.
Statutory Declaration of Haydn Llewellyn, filed on Sep. 8, 2014 in New Zealand Application No. 600480.
Second Amended Notice of Opposition to Grant a Patent, filed on Sep. 8, 2014 in New Zealand Application No. 600480.
Amended Statement of Case, filed on Sep. 8, 2014 in New Zealand Application No. 600480.
Amended Counterstatement, filed on Oct. 15, 2014 in New Zealand Application No. 600480.
Third Amended Notice of Opposition to Grant of Patent, filed on Oct. 21, 2014 in New Zealand Application No. 591993567.
Third Amended Statement of Case, filed on Oct. 21, 2014 in New Zealand Application No. 591993.
Statutory Declaration of Ian Malcolm Smith filed on May 28, 2015 in New Zealand Application No. 591993.
Statutory Declaration of Professor Geoffrey Mark Shaw filed on May 28, 2015 in New Zealand Application No. 591993.
Statutory Declaration of Haydn Llewellyn filed on Sep. 25, 2015 in New Zealand Application No. 591993.
Affirmation of Yi-Cheng Sun filed on Feb. 9, 2016 in New Zealand Application No. 591993.
Affirmation of Dr. David Maurice Rapoport filed on Feb. 9, 2016 in New Zealand Application No. 591993.
First Amended Notice of Opposition to Grant of Patent, filed on Mar. 29, 2016 in New Zealand Application No. 700746.
Amended Statement of Case No. NZ 700746 dated Mar. 2, 2017.
Proceeding Correspondence in NZ Appln. No. 591993 dated Oct. 30, 2017 (1 page).
Applicant's Response to Examiners Report on Latest Proposed Claim Amendments in NZ Appln. No. 591993 dated Oct. 24, 2017 (4 pages).
Amended Claims in Applicant's Response to Examiners Report on Latest Proposed Claim Amendments in NZ Appln. No. 591993 dated Oct. 24, 2017 (3 pages).
Examiners Report on Revised Proposed Claim Amendments in NZ Appln. No. 5919933 dated Sep. 25, 2017 (4 pages).
Proceeding Correspondence in NZ Appln. No. 700746 dated Oct. 3, 2017 (1 page).
Applicant's Response to Examiner Report on Proposed Claim Amendments in NZ Appln. No. 591993 dated Oct. 24, 2017 (4 pages).
Applicant's Response to Examiners Report on Proposed Claim Amendments in NZ Appln. No. 700746 dated Sep. 28, 2017 (1 page).
Amended Claims in Applicant's Response to Examiners Report on Proposed Claim Amendments in NZ Appln. No. 700746 dated Sep. 28, 2017 (3 pages).
Proceeding Correspondence in NZ Appln. No. 700746 dated Sep. 19, 2017 (2 pages).
Response to Examiner's Report in in NZ Appln. No. 591993 dated Aug. 18, 2017 (2 pages).
Amended Claims Response to Examiner's Report in in NZ Appln. No. 591993 dated Aug. 18, 2017 (3 pages).
Proceeding Correspondence in NZ Appln. No. 591993 dated Aug. 28, 2017 ( 1 page).
Proceeding Correspondence in NZ Appln. No. 591993 dated Jul. 20, 2017 (1 page).
Examiners Report on Amendments in Proceeding Correspondence in NZ Appln. No. 591993 dated Jul. 20, 2017 (2 pages).
Claims in Examiners Report on Amendments in Proceeding Correspondence in NZ Appln. No. 591993 dated Jul. 20, 2017 (3 pages).
Proceeding Correspondence in Amended Counterstatement in NZ Appln. No. 700746 dated Jun. 26, 2017 (1 page).
Amended Counterstatement in NZ Appln. No. 700746 dated Jun. 26, 2017 (14 pages).
Amended Claims in Amended Counterstatement in NZ Appln. No. 700746 dated Jun. 26, 2017 (3 pages).
Request for Change of Inventorship Declined in NZ Appln. No. 711441 dated Feb. 16, 2017 (2 pages).
Response to Request for Change of Inventorship Declined in NZ Appln. No. 711441 dated Feb. 27, 2017 (1 page).
Request for Change of Inventorship Declined in NZ Appln. No. 711441 dated Mar. 9, 2017 (1 pages).
Response to Declining of Change of Inventorship dated in NZ Appln. No. 711441 Mar. 14, 2017 (2 pages).
Correspondence re Correction of Error in NZ Appln. No. 711441 dated May 10, 2017 (2 pages).
Correspondence re Request for Correction of Error in NZ Appln. No. 711441 dated Mar. 30, 2017 (1 page).
Declaration in Support of Correspondence re Request for Correction of Error in NZ Appln. No. 711441 dated May 10, 2017 (2 pages).
Correspondence re Applicant's Proposed Claim Amendments in NZ Appln. No. 591993 dated May 15, 2017 (2 pages).
Applicant's Proposed Claim Amendments in NZ Appln. No. 591993 dated May 15, 2017 (3 pages).
First Examination Report in NZ Appln. No. 729116 dated May 22, 2017 (3 pages).
Further Examination Report in NZ Appln. No. 711441 dated May 22, 2017 (2 pages).
USPTO Patent Trial and Appeal Board in Case IPR2016-01723 dated Mar. 9, 2017 (18 pages).
International Search Report for PCT/AU2006/001169, dated Nov. 29, 2006.
Office Action for European Application No. 06126895.9, dated Oct. 29, 2012.
Office Action for U.S. Appl. No. 13/032,178, dated Feb. 6, 2014.
Kwok, U.S. Appl. No. 60/656,880, filed Mar. 1, 2005.
Kwok, U.S. Appl. No. 60/707,950, filed Aug. 15, 2006.
Japanese Office Action issued in JP 2006-344662 dated Nov. 22, 2011 with English Translation.
Examiner's First Report issued in related Australian Application No. 2006220222 (dated Nov. 8, 2010).
Office Action issued in related Japanese Application No. 2007-557276 (dated May 10, 2011) with English Translation.
Office Action issued in related European Application No. 06704913.0 (dated Oct. 20, 2011).
International Search Report for PCT/AU2006/000238 dated Apr. 26, 2006.
Supplementary Partial European Search Report for EP 06704913 dated Oct. 20, 2011.

(56) References Cited

OTHER PUBLICATIONS

International Preliminary Report on Patentability for PCT/AU/2006/000238 dated Sep. 11, 2007.
Written Opinion for PCT/AU2006/000238 dated Apr. 20, 2006.
4th Amended Statement of Case in NZ appplication No. 591993 dated Apr. 13, 2018 (17 pages).
International Standard, IEC 60601-1-8, First Edition, dated Aug. 2003 (78 pages).
Pulmonetic Systems Innovations for Life, LTV Series Ventilators Operators Manual, dated Apr. 2004 (282 pages).
Proceeding Correspondence in Application No. 591993 dated Apr. 24, 2018 (2 pages).
Third Amended Notice of Opposition and Second Amended Statement of Case in NZ Application No. 700746 dated Jan. 23, 2018 (2 pages).
Second Amended Statement of Case dated Jan. 23, 2018 (20 pages).
Proceeding Correspondence in Application No. 591993 dated Jan. 31, 2018 (2 pages).
Response to Applicant's Proposed Amendments in Application No. 700746 dated Oct. 5, 2018 (4 pages).
Proceeding Correspondence in NZ Application No. 700746 dated Nov. 8, 2018 (3 pages).
Proceeding Correspondence in NZ Application No. 700746 dated Aug. 10, 2018 (3 pages).
Response to Applicant's Proposed Amendments in NZ Application No. 700746 dated Aug. 3, 2018 (2 pages).
First Examination Report in NZ Application No. 747190 dated Oct. 16, 2018 (3 pages).
Office Action in U.S. Appl. No. 14/665,192 dated Jul. 27, 2017 (26 pages).
U.S. Appl. No. 60/656,880, filed Mar. 1, 2005 (26 pages).
U.S. Appl. No. 60/703,432, filed Jul. 29, 2005 (26 pages).

\* cited by examiner

| Mask Type | Resistance Detected |
|---|---|
| Activa® | 1 ohm |
| Mirage® | 2 ohm |
| UltraMirage® | 3 ohm |

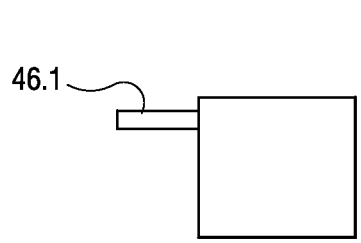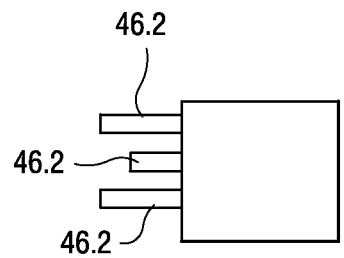
Fig. 12        Fig. 13
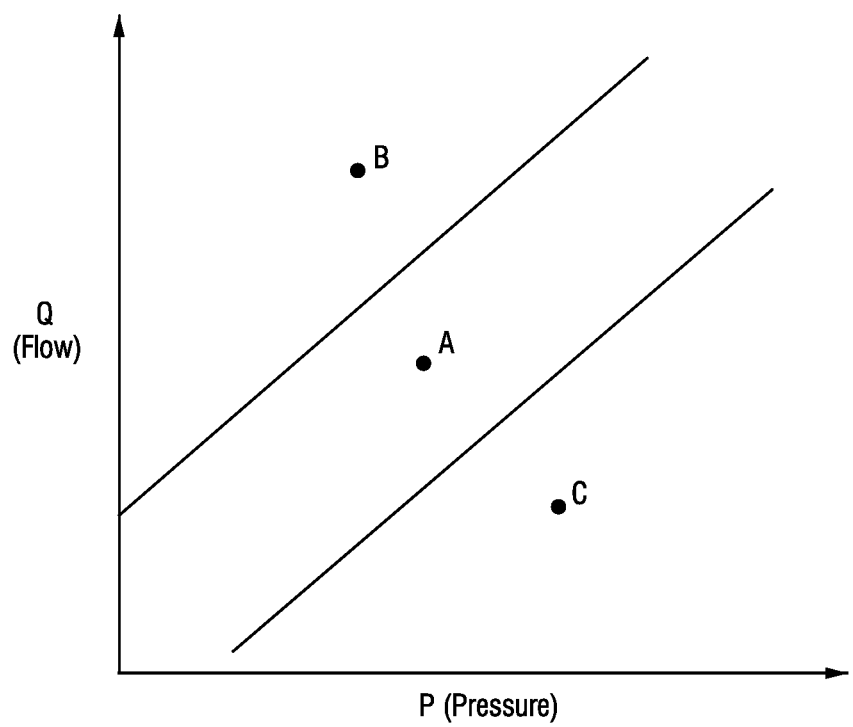
Fig. 14

RECOGNITION SYSTEM FOR AN APPARATUS THAT DELIVERS BREATHABLE GAS TO A PATIENT

CROSS REFERENCE TO RELATED APPLICATION

This application is a continuation of Ser. No. 13/588,556, filed Aug. 17, 2012, which is a divisional of application Ser. No. 11/794,150, filed Oct. 29, 2008 (now Pat. No. 8,267,084, issued Sep. 18, 2012), which is a national stage of International Application No. PCT/AU2006/000238, under 35 U.S.C. 371, filed Feb. 24, 2006, which claims the benefit of provisional Application No. 60/656,880, filed Mar. 1, 2005, the entire contents of each being hereby incorporated by reference in this application.

FIELD OF THE INVENTION

The present invention relates to an apparatus that delivers breathable gas to a patient.

BACKGROUND OF THE INVENTION

Apparatus to deliver breathable gas to a patient typically includes a flow generator, an air delivery conduit, and a patient interface. Prior to use, operating parameters of the flow generator, e.g., treatment pressure, need to be manually adjusted by the patient to coordinate with the peripheral components, e.g., patient interface, being used. For example, known flow generators include a menu system that allows the patient to select the type of peripheral components being used, e.g., by brand, method of delivery, etc. Once the components are selected by the patient, the flow generator can select appropriate operating parameters of the flow generator that best coordinate with the selected components.

The present invention provides improvements to known apparatus to facilitate the coordination between the flow generator and the peripheral components.

SUMMARY OF THE INVENTION

One aspect of the invention is directed towards a recognition system that provides structure to facilitate the coordination between the flow generator and the peripheral components.

Another aspect of the invention relates to an adapter for use with a flow generator that generates a supply of pressurized air to be provided at an outlet to a patient for treatment. The adapter includes a conduit attachable to the outlet of the flow generator, and an identifying element supported by the conduit and providing an identifying feature unique to a specific peripheral component attachable to the flow generator. The identifying feature is communicatable to the flow generator so that appropriate operating parameters of the flow generator may be automatically selected by the flow generator to coordinate with the specific peripheral component.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate, an understanding of the various embodiments of this invention. In such drawings:

FIGS. 12 and 13 illustrate schematic side views of adapters/connectors according to further embodiments of the present invention;

FIG. 14 is a graph illustrating upper and lower ranges preferred by manufacturers of patient interfaces for flow vs. pressure.

DETAILED DESCRIPTION OF ILLUSTRATED EMBODIMENTS

Figure 1:
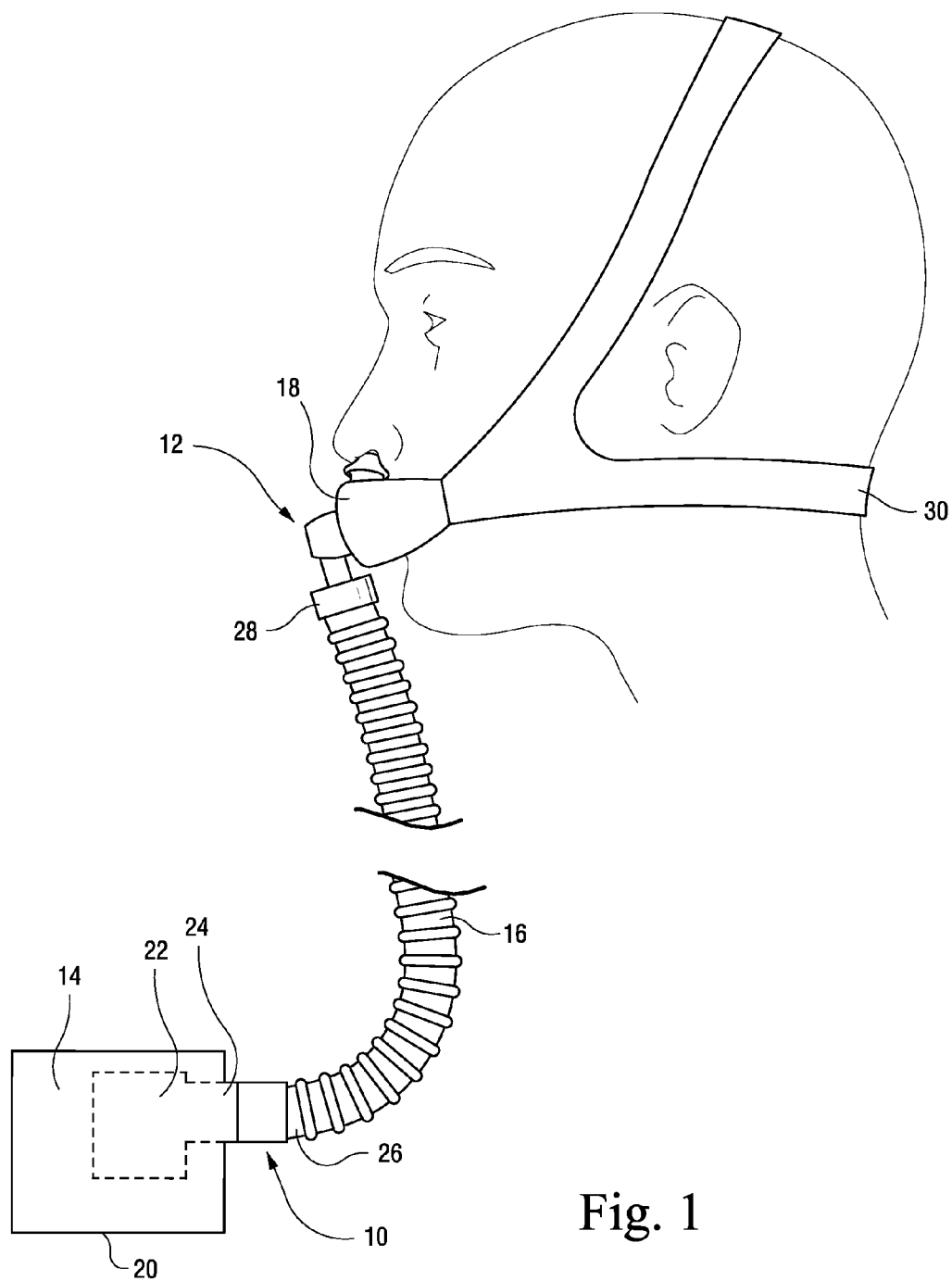
FIG. 1 is a side view of an embodiment of an apparatus that delivers breathable gas to a patient, the apparatus including a recognition system constructed according to an embodiment of the present invention.

FIGS. 1-9 illustrate a recognition system 10 constructed according to an embodiment of the present invention. The recognition system 10 is structured for use with an apparatus 12 that delivers a supply of pressurized breathable air to a patient for treatment, e.g., of Sleep Disordered Breathing (SDB) with CPAP or Non-Invasive Positive Pressure Ventilation (NIPPV). As best shown in FIG. 1, the apparatus 12 generally includes a flow generator 14, an air delivery conduit 16, and a patient interface 18. As discussed in greater detail below, the recognition system 10 allows the flow generator 14 to automatically recognize or identify one or more of the peripheral components selected by the patient so that appropriate operating parameters of the flow generator 14 may be automatically selected by the flow generator 14 to coordinate with the selected peripheral components.

The flow generator 14 is structured to generate a supply of pressurized air to be provided to a patient for treatment. The flow generator 14 includes a housing 20 and a blower 22 supported within the housing 20. As is known in the art, the blower 22 is operable to draw a supply of air into the housing 20 through one or more intake openings and provide a pressurized flow of air at an outlet 24 (see FIGS. 1, 4, and 5).

The supply of pressurized air is delivered to the patient via the air delivery conduit 16 that includes one end 26 coupled to the outlet 24 of the flow generator 14 and an opposite end 28 coupled to the patient interface 18, as shown in FIG. 1.

The patient interface 18 comfortably engages the patient's face and provides a seal. The patient interface 18 may have any suitable configuration as is known in the art, e.g., full-face mask, nasal mask, oro-nasal mask, mouth mask, nasal prongs, etc. Also, any suitable headgear arrangement 30 may be utilized to comfortably support the patient interface 18 in a desired position on the patient's face.

Figure 2:
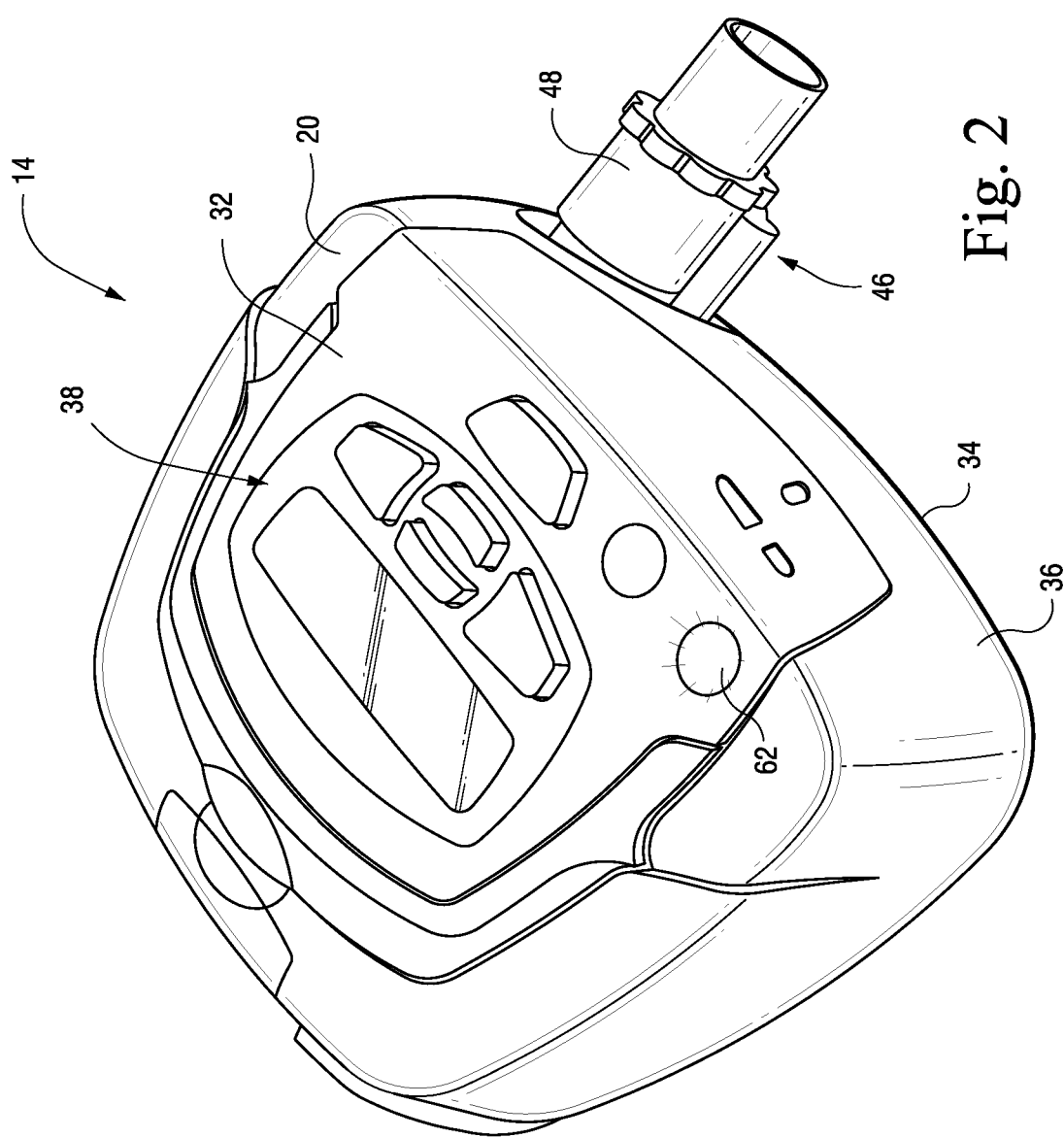
FIG. 2 is a top perspective view illustrating a flow generator incorporating the recognition system shown in FIG. 1, and one of the indicator lights being activated.
Figure 3:
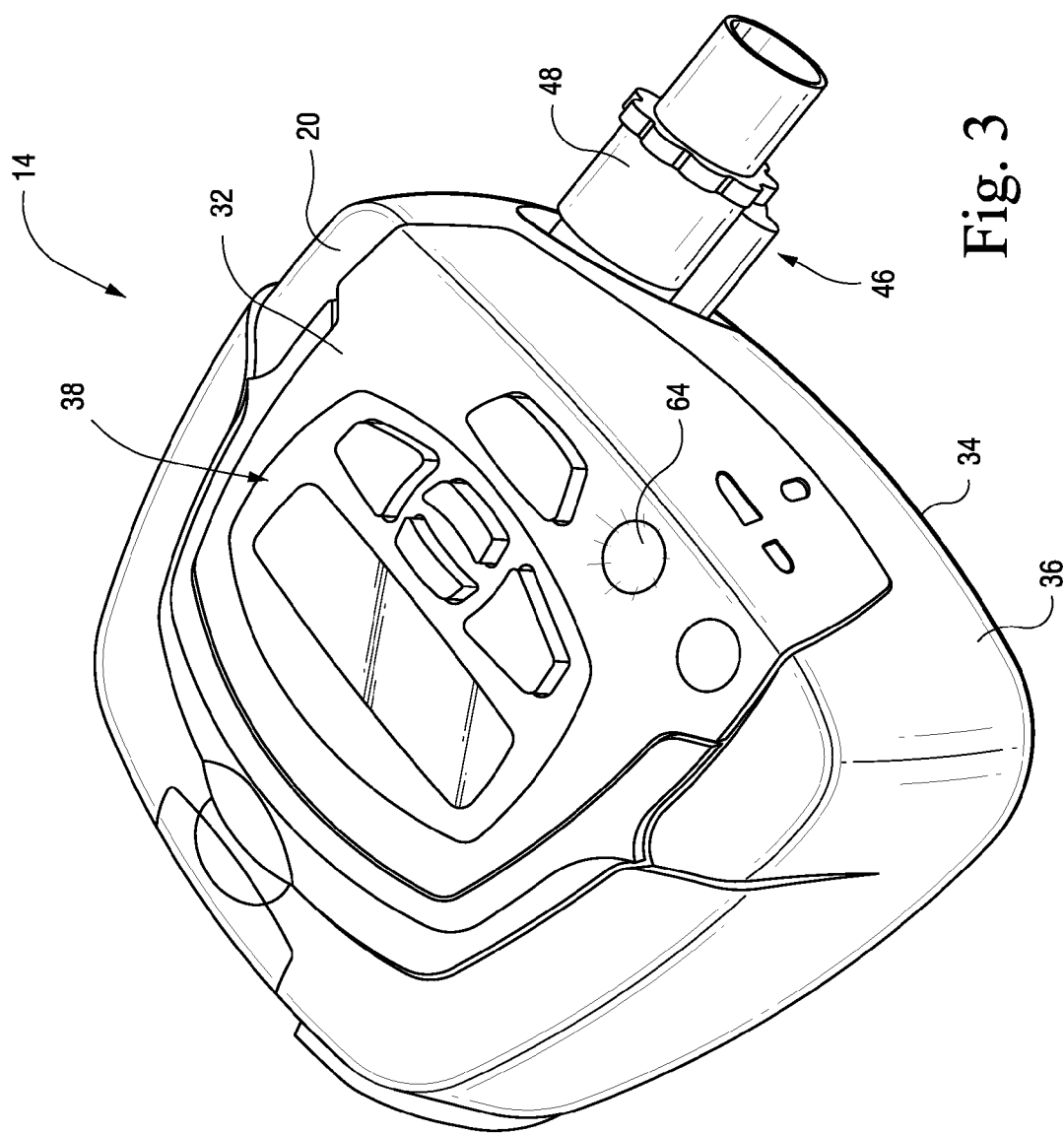
FIG. 3 is a top perspective view similar to FIG. 2 with another of the indicator lights being activated.
Figure 4:
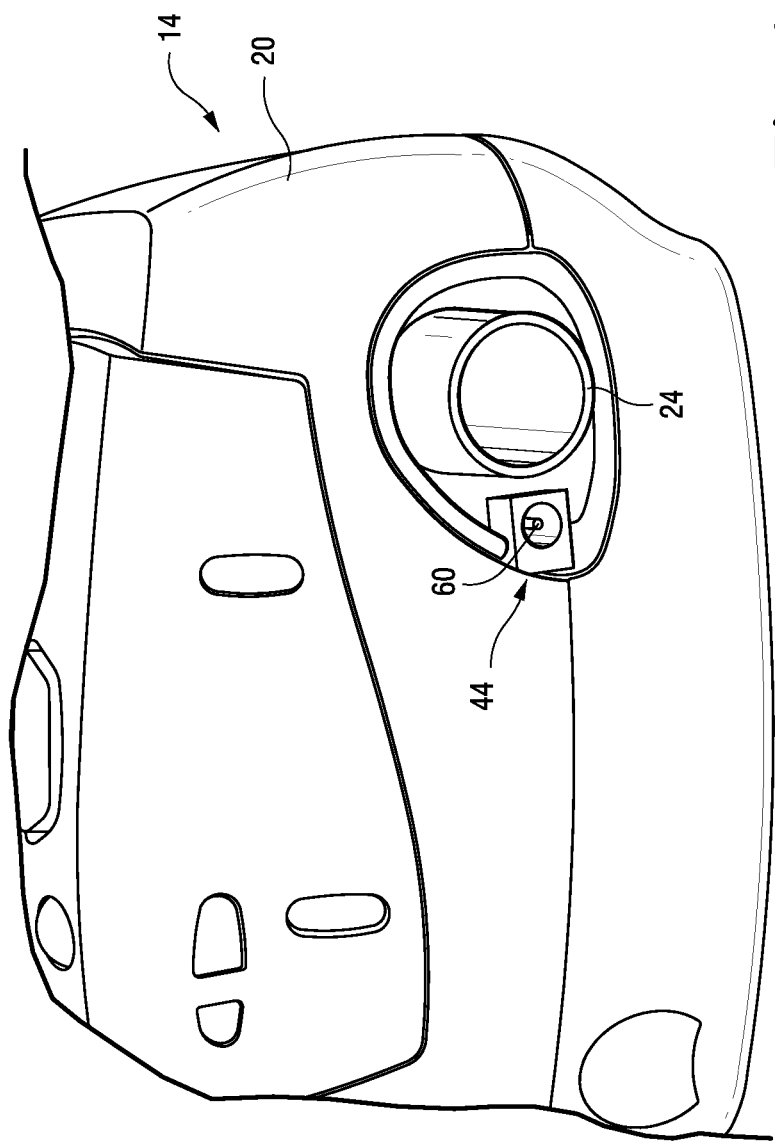
FIG. 4 is a front perspective view of the flow generator shown in FIG. 2 with an adapter of the recognition system removed.
Figure 5:
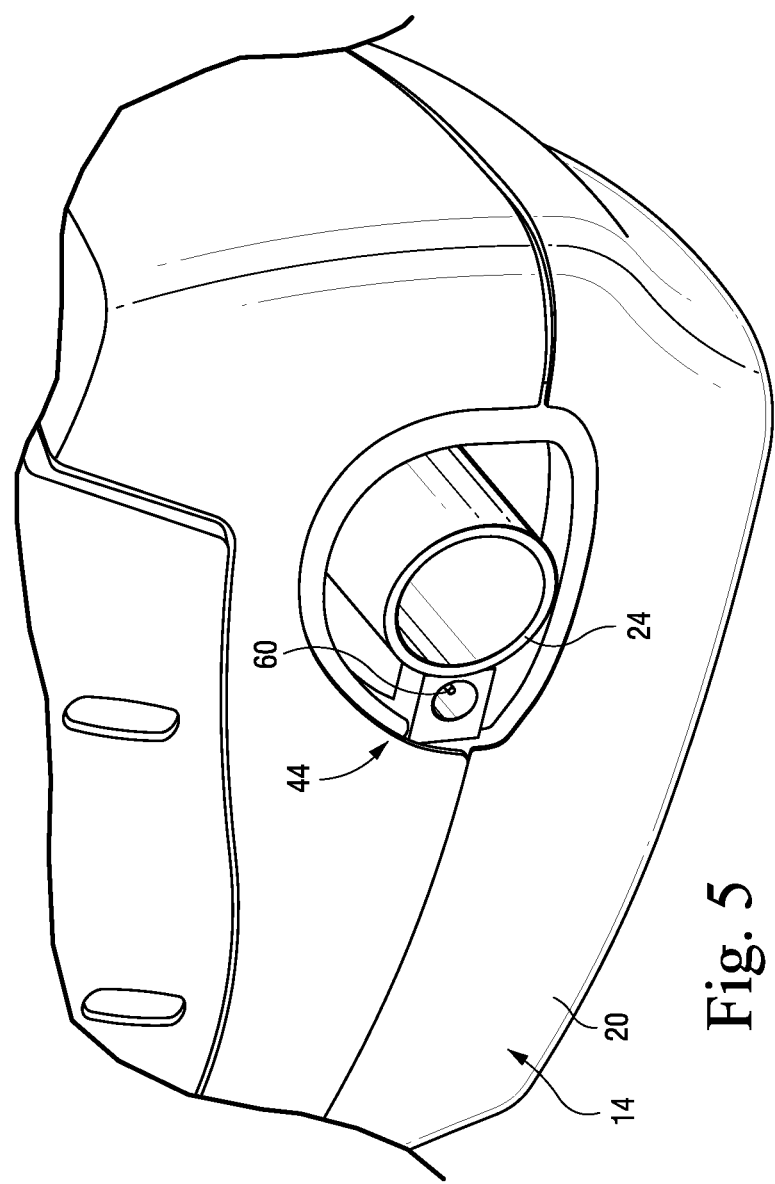
FIG. 5 is an enlarged front perspective view of the flow generator shown in FIG. 4.

As best shown in FIGS. 2-4, the housing 20 of the flow generator 14 includes an upper wall 32, a lower wall 34, and side walls 36 that interconnect the upper and lower walls 32, 34. In the illustrated embodiment, the outlet 24 is provided in one of the side walls 36. Also, the upper wall 32 incorporates a manual control unit 38 for adjusting one or more parameters of the flow generator 14, e.g., treatment pressure. However, the outlet 24 and/or control unit 38 may be incorporated into any of the walls of the housing 20. Also, it should be understood that the flow generator 14 may include additional features incorporated into the housing 20, e.g., power supply.

Figure 6:
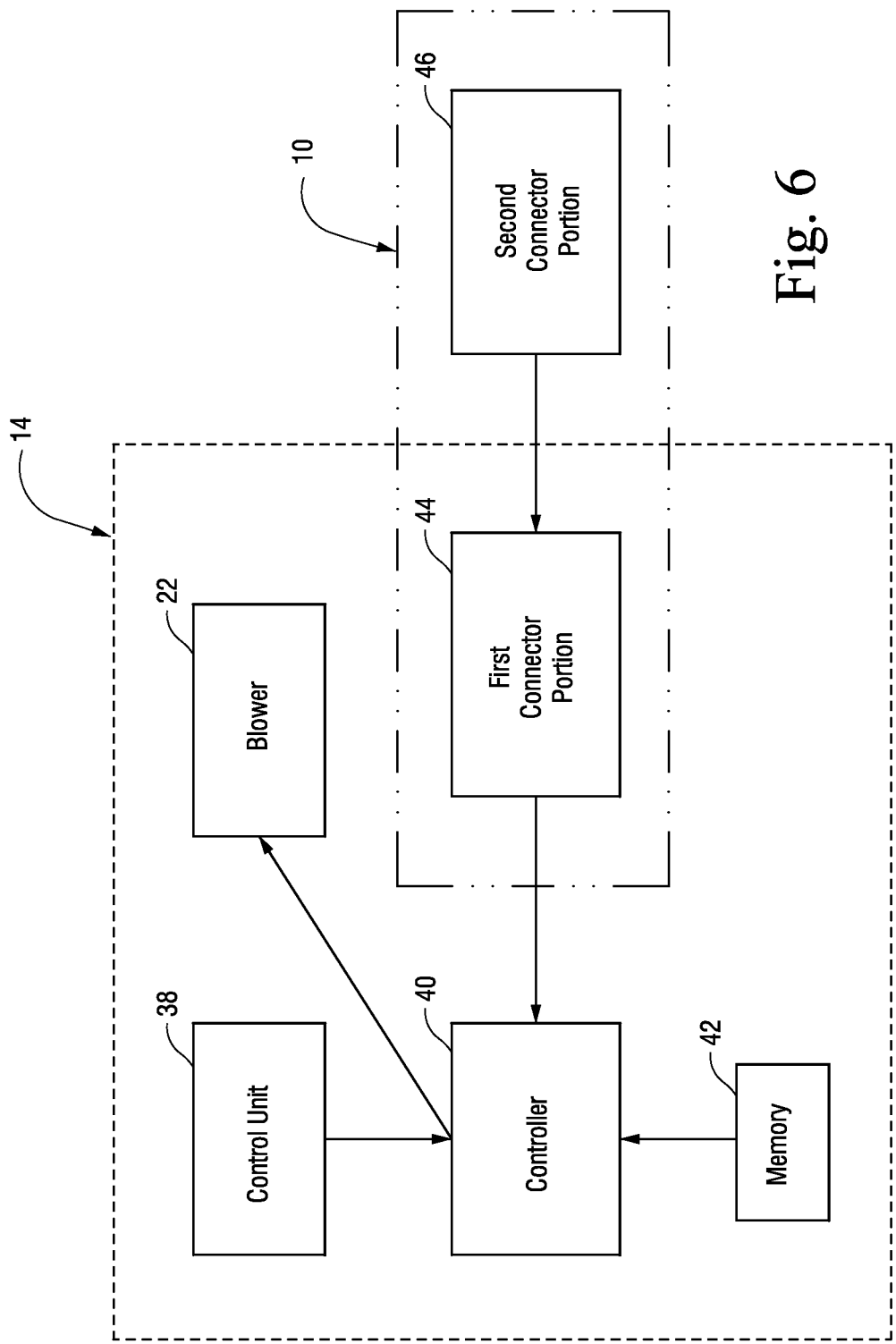
FIG. 6 is a schematic diagram of the flow generator and recognition system shown in FIG. 2.
Figure 7:
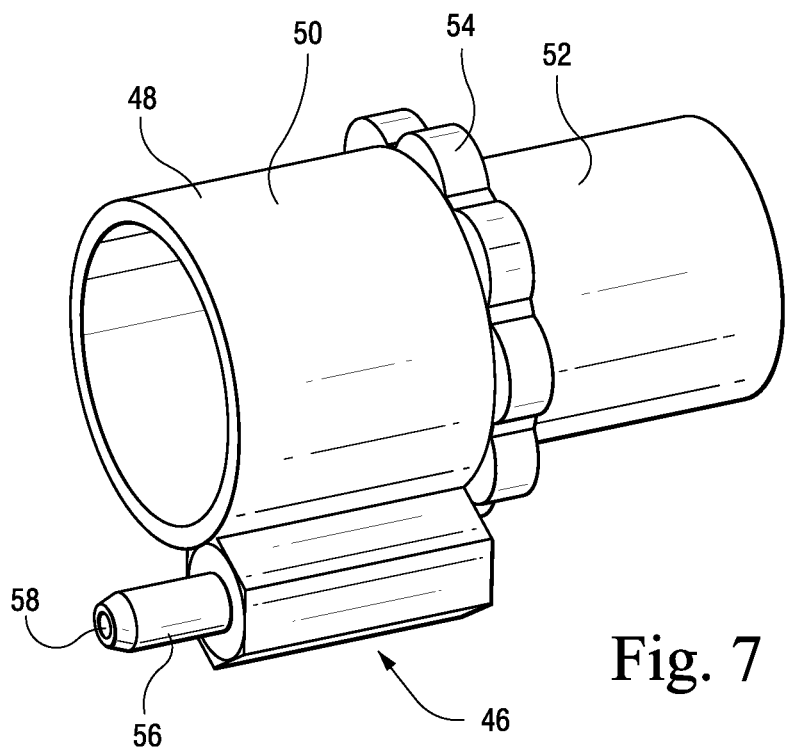
FIG. 7 is a perspective view of an adapter of the recognition system shown in FIG. 2.
Figure 8:
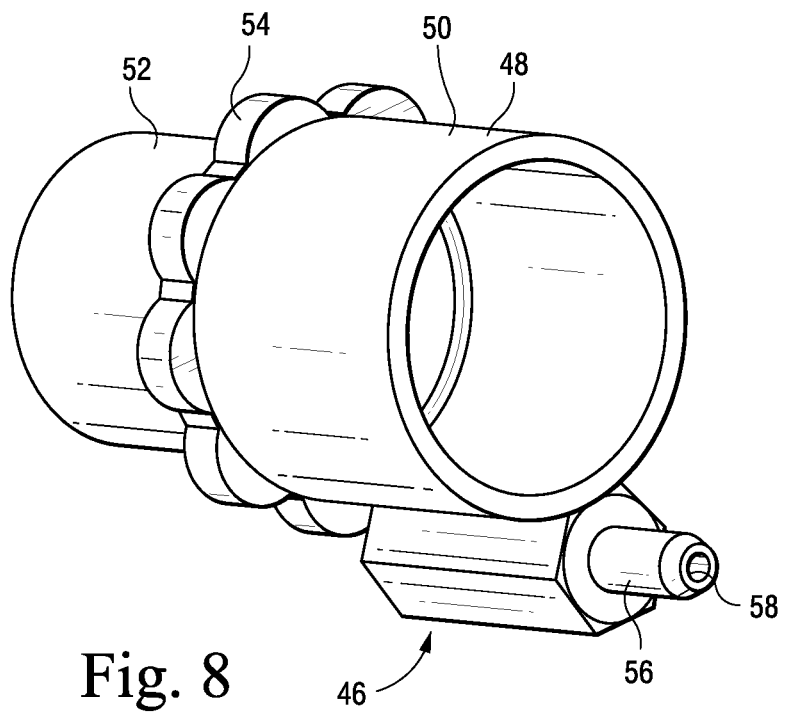
FIG. 8 is a perspective view, from a different angle, of the adapter shown in FIG. 7.

As shown in FIG. 6, the flow generator 14 includes a controller 40 operable to receive input signals and to control operation of the blower 22 based on input signals. Input signals may be provided by the control unit 38 which has a plurality of control features that can be manually selected by the patient to adjust various parameters of the flow generator 14. For example, the patient may select the type of patient interface 18 being used, e.g., via a menu system of the control unit 38, so that the controller 40 can adjust the blower outlet pressure so that it coordinates with the selected patient interface 18. The controller 40 may include a memory 42 that stores preferred operating parameters for a variety of patient interfaces, e.g., by brand or method of delivery. When the controller 40 receives the input signal regarding the selected patient interface 18 from the control unit 38, the controller 40 can operate the blower 22 based on the stored operating parameters in the memory 42 for the selected patient interface 18. Alternatively, the preferred operating parameters for a selected patient interface 18 may be entered manually through the control unit 38.

Connector Recognition

The recognition system 10 is provided to allow the controller 40 of the flow generator 14 to automatically recognize one or more peripheral components, e.g., the patient interface 18, so that the patient does not have to utilize the control unit 38. Moreover, the recognition system 10 may allow the apparatus 12 to operate more efficiently as the recognition system 10 enables the flow generator 14 to select operating parameters that are specifically optimized for the selected peripheral components.

In the illustrated embodiment, the recognition system 10 includes a first connector portion 44 provided by the flow generator 14 (e.g., see FIGS. 4, 5, and 6), and a second connector portion 46 adapted to be removably coupled with the first connector portion 44 (e.g., see FIGS. 2, 3, and 6-9). The second connector portion 46 is associated with a specific peripheral component, e.g., patient interface 18, and includes an identifying feature unique to the specific peripheral component. The first connector portion 44 includes structure to communicate the identifying feature of the second connector portion 46 to the controller 40 so that the controller 40 can recognize the identifying feature and hence the associated peripheral component. The controller 40 can then select appropriate operating parameters of the blower 22, e.g., via memory 42, to coordinate with the associated peripheral component. For example, the blower 22 may be controlled so that the blower outlet pressure is relatively lower for one group of patient interfaces, e.g., nasal, and relatively higher for another group of patient interfaces, e.g., nasal and mouth.

As shown in FIGS. 2, 3, and 7-9, the second connector portion 46 is provided on an adapter 48 that is adapted to interconnect the outlet 24 of the flow generator 14 and the end 26 of the air delivery conduit 16. Specifically, the adapter 48 is in the form of a conduit including a first end portion 50 attachable to the outlet 24 and a second end portion 52 attachable to the air delivery conduit 16. As illustrated, first end portion 50 has a greater diameter than the second end portion 52. However, the end portions 50, 52 may have any suitable arrangement, e.g., similar diameters. Also, a gripping portion 54, in the form of spaced contoured ribs, is provided between the first and second end portions 50, 52 to facilitate connection.

As illustrated, the second connector portion 46 is mounted to the first end portion 50. As a result, the second connector portion 46 is able to removably couple with the first connector portion 44 on the flow generator 14 when the adapter 48 is coupled to the outlet 24. In the illustrated embodiment, the first connector portion 44 is in the form of a first conductor and the second connector portion 46 is in the form of a second conductor. Also, the second conductor 46 is bridged with an identifying element, in the form of a resistor, that provides the identifying feature unique to a specific peripheral component.

In use, the adapter 48 is attached to the outlet 24 so that the second conductor 46 is electrically coupled to the first conductor 44. In the illustrated embodiment, the second conductor includes a metallic pin 56 with an axially extending opening 58 and the first conductor includes a metallic pin 60. The axially extending opening 58 of the metallic pin 56 receives the metallic pin 60 therein to electrically couple the first and second conductors 44, 46. However, the first and second conductors 44, 46 may be electrically coupled in any other suitable manner. Once coupled, the controller 40 can detect the resistance provided by the resistor bridged with the second conductor 46. The resistance is unique to a particular peripheral component so the controller 40 can recognize the specific peripheral component by the resistance. Once recognized, the appropriate operating parameters of the flow generator 14 can be automatically selected by the controller 40 to coordinate with the specified peripheral component.

Figures 9, 10:
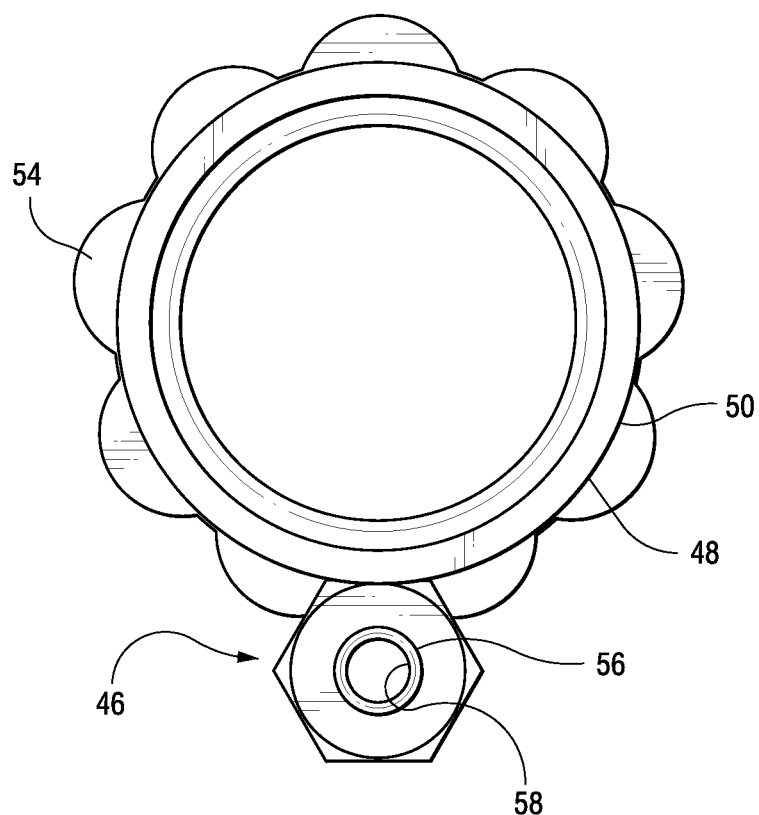
FIG. 9 is a top view of the adapter shown in FIG. 7.
FIG. 10 is a chart illustrating various magnitudes of resistance detected by the recognition system shown in FIG. 2 for embodiments of adapters associated with known masks sold by ResMed Ltd.

For example, FIG. 10 lists three known patient interfaces sold by ResMed Ltd. Each of the patient interfaces is supplied with an adapter 48 having a second connector portion 46 with a unique resistance value. In the illustrated embodiment, the Activa® has a resistor that provides resistance of about 1 ohm, the Mirage® has a resistor that provides resistance of about 2 ohm, and the UltraMirage® has a resistor that provides resistance of about 3 ohm. Accordingly, if the controller 40 detects a 2 ohm resistance when the adapter 48 and second connector portion 46 thereof is engaged with the flow generator 14, the controller 40 will recognize that the Mirage® is coupled to the flow generator 14 and select blower operating parameters that are optimized for the Mirage®.

Thus, the recognition system 10 provides a "plug and play" arrangement wherein the patient can simply couple the adapter 48 and second connector portion thereof 46 to the flow generator 14 to automatically configure the flow generator 10 for a particular peripheral component, e.g., patient interface 18.

It should be understood that more than one peripheral component of the apparatus 12 may be provided with a unique adaptor 48 that automatically configures the flow generator 14 for the associated peripheral component. For example, an adapter 48 may be provided with each of the patient interface 18, air delivery conduit 16, and humidifier (not shown) coupled to the flow generator 14. Each adapter 48 would have a unique identifying feature, as described above, so that the controller 40 can recognize which components are coupled to the flow generator 14. Moreover, the controller 40 can optimize operation of the flow generator 14 to take into account the features of each of the patient interface 18, air delivery conduit 16, humidifier.

In one embodiment, the adapters 48 may be color coded to correspond with particular peripheral components. Moreover, the peripheral component may have a colored element that matches the color of the corresponding adapter 48. This allows the adapters 48 to be easily recognized and associated with the respective component. For example, a patient interface 18 may have a purple colored swivel connector that is accompanied by a purple colored adapter 48. When the purple colored adapter 48 is coupled to the flow generator 14, the controller 40 will optimize the flow generator 14 to correspond with the features of the purple colored patient interface 18. In addition, or in the alternative, the connector and/or peripheral component may have a tactile indicator such as shape, e.g., a polygon, hexagon, etc.

Figure 11:
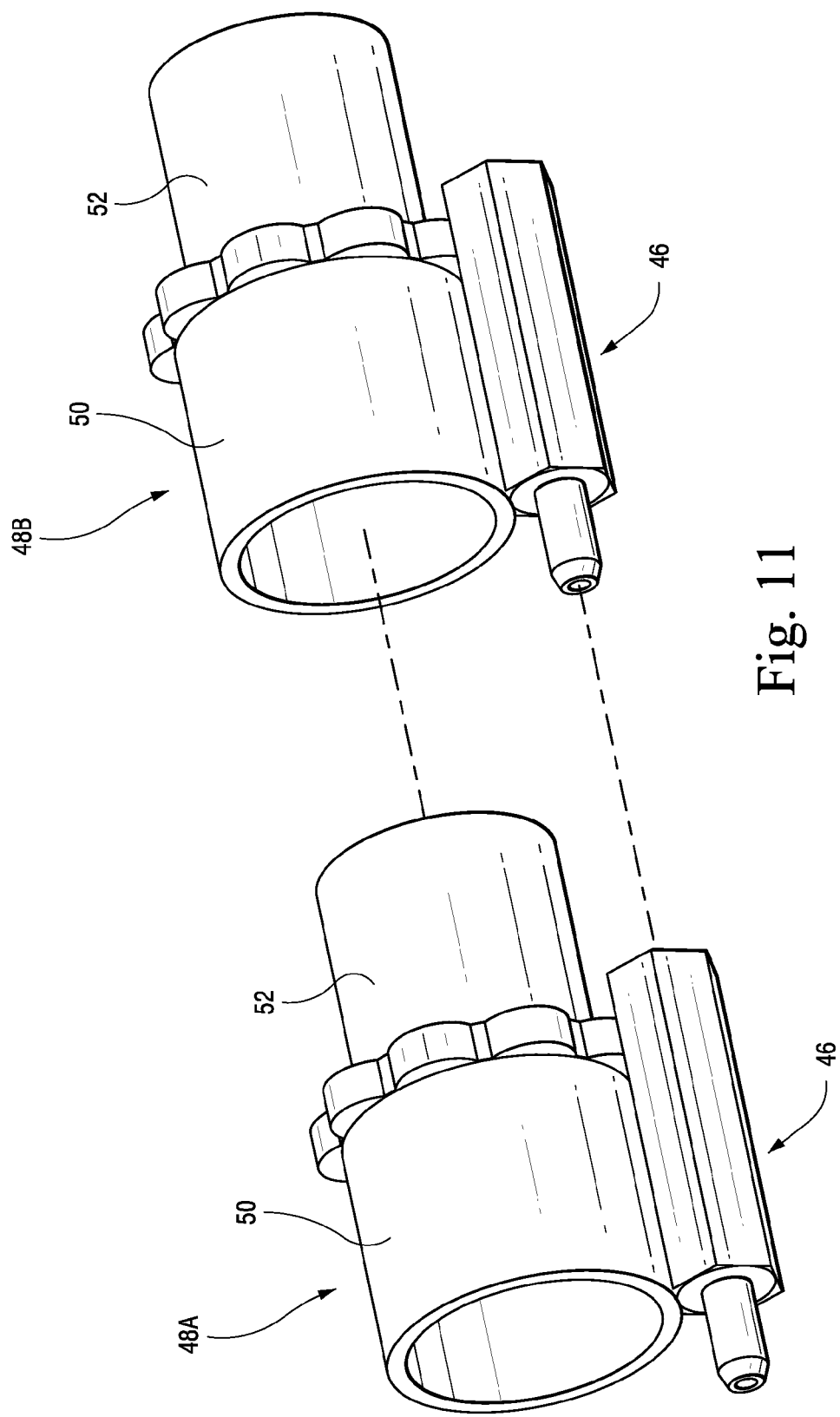
FIG. 11 is a perspective view illustrating stacked adapters of the recognition system.

When multiple peripheral components are coupled to the flow generator 14, e.g., patient interface and humidifier, multiple adapters 48 may be stacked to the outlet 24 of the flow generator 14. For example, a purple adapter 48 associated with a patient interface 18 piggybacked to a yellow adapter 48 associated with a humidifier would signal the controller 40 that both a patient interface 18 and humidifier are attached to the flow generator 14. When piggybacked, one of the adapters 48A is coupled to the flow generator 14 as discussed above and the second adapter 48B is coupled to the first adapter 48A such that the first end portion 50 of the second adapter 48B is attachable to the second end portion 52 of the first adapter 48A and the second end portion 52 of the second adapter 48B is attachable to the air delivery conduit 16 as shown in FIG. 11. Moreover, the conductor 46 of the second adapter 48B is electrically coupled to a rear portion of the conductor 46 of the first adapter 48A. In one embodiment, the adapter 48B may be structured such that it cannot receive a plug from a downstream connector, rather it can only plug into the adapter 48A closer to the flow generator, so as to impose a limitation on the order of attachment. However, it is preferred that the adapters can be attached in random order, to facilitate the connector assembly operation.

The piggyback value of two resistor values wired in parallel could be recognized via simple electronics (e.g., 1/R Total=$1/R_1+1/R_2$, where $R_1$ is the resistor value associated with the patient interface and $R_2$ is the resistor value associated with the humidifier). The value of (1/R Total) would relate to a blower setting that adjusts the operating parameters to function optimally with the specific features of both the selected patient interface and humidifier. This arrangement eliminates user intervention to match peripheral components for optimal performance of the connected system.

It should be understood that the recognition system 10 may have any suitable structure to enable the controller 40 to automatically recognize selected peripheral components. In the illustrated embodiment, an adapter 48 incorporating an identifiable resistor is utilized to identify the peripheral component. However, the identifying element may have any suitable identifiable structure, e.g., impedance (e.g., using holes of various sizes), microswitches, infrared detectors, variable length pins, variable number of pins, variable pin mountings, spring loads, etc. For example, one embodiment may incorporate one or more variable length pins 46.1 on the end of the connector that can either incorporate a microswitch (or series of switches depending on length) or operate a variable resistor whose value is determined by the length of the pin, e.g., how far the pin pushes a lever operating variable resistor. A series of microswitches, e.g., 6 switches, located around the connector could be operated by pins 46.2 to either the on or off position, similar to a remote control. See, e.g., FIGS. 12 and 13.

Alternatively, the adaptor and/or a component thereof such as a pin may include a coded portion that encodes the flow generator with the peripheral component. This is similar to how a camera film housing encodes the camera with the camera film, upon loading of the housing into the camera.

In another embodiment, the second connector portion 46 may be provided as a separate key, separate from the adapter 48, that is engagable with the first connector portion 44 provided on the flow generator 14. Thus, the adapter 48 may be eliminated and the air delivery conduit 16 may connect directly to the outlet 24 of the flow generator 14.

Also, the controller 40 may identify the peripheral component in any suitable manner. That is, an identifying feature associated with the peripheral component may be communicated to the controller 40 in any suitable manner. For example, the identifying feature may be incorporated into the peripheral component, e.g., patient interface, itself and be communicated to the controller 40 via a wire extending from the peripheral component to the flow generator 14. Alternatively, the identifying feature may be communicated to the controller 40 wirelessly, e.g., RFID, IR, prismatic, smart card (computer chip). In "wireless" embodiments, the controller 40 would be coupled to a receiver adapted to receive signals transmitted by the identifying component associated with the peripheral component.

In another embodiment, the peripheral component may include a bar code with identifying information so that the peripheral component may be moved past a bar code reader provided on the flow generator 14 that will allow the controller 40 to identify the specific peripheral component being utilized.

Also, other information may be provided by the identifying component, e.g., a log of the patient's use, components used during each use, end of life service indication, etc.

The flow generator 14 may include one or more indicator lights to indicate that the peripheral components have been recognized and/or identified. For example, as shown in FIGS. 2 and 3, the flow generator 14 includes a red light 62 that indicates that the component has not yet been recognized (FIG. 2), and a green light 64 that indicates that the adapter 48 is connected and the associated component has been recognized. Thus, the indicator lights may provide positive feedback regarding connection and blower set-up status. The different lights may also indicate different peripherals and confirm correct alignment, e.g., one light for an Activa® mask, another light for an UltraMirage® Full Face Mask, etc.

In the illustrated embodiment, the adapter 48 must be properly aligned with the outlet 24 and the first connector portion 44 to enable the second connector portion 46 to couple with the first connector portion 44. However, the first and second connector portions 44, 46 may be configured and arranged so orientation of the adapter 48 with respect to the outlet 24 does not matter. Moreover, the flow generator will continue to operate even if one or more components of the recognition system are not employed, although the operating characteristics may not be optimized for the particular component in use.

The recognition system 10 is advantageous in that it allows the flow generator 14 to be optimized to function with the connected peripheral components. This minimizes patient intervention to setup the flow generator 14, and therefore improves ease of use.

Leak Testing on Manufacturer Line

Figure 15:
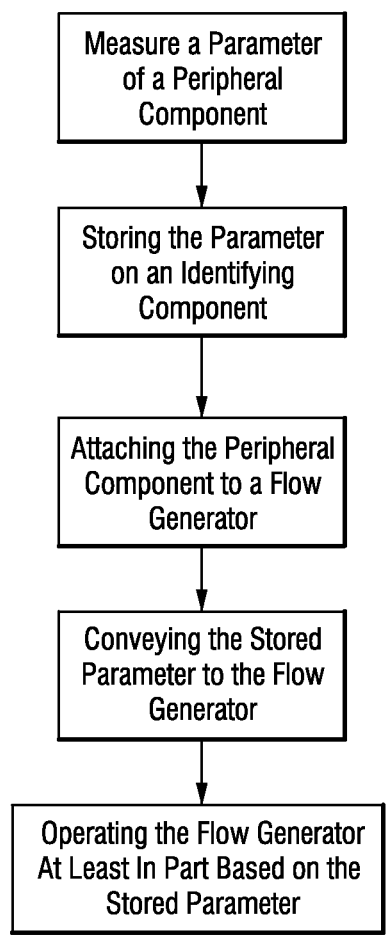
FIG. 15 is a flow chart illustrated an embodiment of a method for operating a flow generator.

Typically, manufacturers test manufactured patient interfaces on the manufacturing line for leak and require that they fall within upper and lower ranges in flow vs. pressure curve to ensure that each patient interface can be used with a flow generator. The flow vs. pressure curve measures for intended, e.g., vents, and Unintended sources of leak. Thus, a patient interface falling at A in FIG. 14 would be acceptable, and patient interfaces falling at B and C in FIG. 14 would not be acceptable. If a recognition system 10 is utilized, the leak testing results of the patient interface may be provided on an identifying component, e.g., smart card, and transferred to the controller 40 in use. FIG. 15 is a flow chart illustrating an exemplary method for operating a flow generator. With this information, the controller 40 can optimize the flow generator 14 to compensate for the measured operating parameter of the patient interface. That is, the specific parameters of the patient interface are compensated at the flow generator 14. This allows the typical range requirements to be eliminated so that masks falling at B and C in FIG. 14 can be utilized. Thus, manufacturing design constraints may be reduced, so that patient interfaces may be used that would not typically be used due to manufacturing standards.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. A continuous positive airway pressure (CPAP) system comprising:
    a flow generator configured to generate a supply of pressurized breathable gas that is delivered, via an airflow path that includes at least an outlet formed in the flow generator, a delivery conduit, and a patient interface, to a patient for treatment, the flow generator including a first connector structure;
    a peripheral CPAP component that is operable to be a component of the CPAP system and assist in application of treatment for the patient;
    a connector removably attachable to the first connector structure and separate from the peripheral CPAP component and, when attached, configured to communicate the pressurized breathable gas delivered from the outlet to other components included in the airflow path, the connector including an identifying element disposed on or in the connector with the identifying element including an identifying feature related to the peripheral CPAP component;
    an electronic controller electronically coupled to the first connector structure and configured to:
        automatically recognize, via the first connector structure, the peripheral CPAP component related to the connector when attached to the first connector structure based on the identifying feature; and
        automatically adjust at least one operating parameter of the flow generator based on recognition of the peripheral CPAP component, where adjustment of the operating parameter changes how the supply of pressurized breathable gas is delivered to the patient.

2. The CPAP system of claim 1, wherein the identifying feature includes data of at least one of the following: a log of patient use, an end of life service indication, components used during each use, and/or a leak parameter that indicates a measured leak value associated with the peripheral CPAP component.

3. The CPAP system of claim 1, wherein the connector has a tactile indicator used to assist in recognizing the peripheral component.

4. The CPAP system of claim 3, wherein the tactile indicator is a polygon or hexagon shape.

5. The CPAP system of claim 1, wherein the identifying feature includes an airflow related parameter of the peripheral CPAP component.

6. The CPAP system of claim 1, wherein the peripheral CPAP component is at least one of the patient interface, the delivery conduit, and a humidifier.

7. The CPAP system of claim 1, where the electronic controller is further configured to:
    responsive to recognition of the peripheral CPAP component as a first type of patient interface, set a pressure level of the pressurized breathable gas to a first level; and
    responsive to recognition of the peripheral CPAP component as a second type of patient interface, which is different from the first type of patient interface, set the pressure level of the pressurized breathable gas to a second level that is higher than the first level.

8. The CPAP system of claim 1, wherein the connector is configured to structurally couple the first connector structure to an end of the delivery conduit.

9. The CPAP system of claim 1, wherein a diameter of a first end of the connector is greater than a diameter of a second, opposing, end of the connector.

10. The CPAP system of claim 1, wherein the identifying element of the connector is a resistor and the identifying feature is a resistance of a resistor.

11. The CPAP system of claim 10, wherein the peripheral CPAP component is the patient interface and a particular resistance of the resistor is associated with a type of patient interface to which the patient interface belongs.

12. The CPAP system of claim 1, wherein the connector is configured to be electrically coupled to the first connector structure when attached.

* * * * *